US00PP25166P2

(12) United States Plant Patent
Ren

(10) Patent No.: US PP25,166 P2
(45) Date of Patent: Dec. 9, 2014

(54) ***CALIBRACHOA* PLANT NAMED 'BALCABPURIM'**

(50) Latin Name: *Calibrachoa×hybrida*
Varietal Denomination: Balcabpurim

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 43 days.

(21) Appl. No.: 13/986,983

(22) Filed: Jun. 20, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell
(74) *Attorney, Agent, or Firm* — Audrey Charles

(57) ABSTRACT

A new and distinct cultivar of *Calibrachoa* plant named 'Balcabpurim', characterized by its deep purple-colored flowers, medium green-colored foliage, and moderately vigorous, trailing growth habit, is disclosed.

1 Drawing Sheet

Latin name of genus and species of plant claimed: *Calibrachoa×hybrida.*

Variety denomination: 'Balcabpurim'.

BACKGROUND OF THE INVENTION

The present invention relates to a new and distinct cultivar of *Calibrachoa* plant botanically known as *Calibrachoa×hybrida* and hereinafter referred to by the cultivar name 'Balcabpurim'.

The new cultivar originated in a controlled breeding program in Elburn, Ill. during June 2008. The objective of the breeding program was the development of *Calibrachoa* cultivars with attractive flower coloration, medium green-colored foliage, and a moderately vigorous, trailing growth habit.

The new *Calibrachoa* cultivar is the result of cross-pollination. The female (seed) parent of the new cultivar is the proprietary *Calibrachoa×hybrida* breeding selection coded 2296-10-1, not patented, characterized by its dark bluish-purple colored flowers, medium green-colored foliage, and vigorous, mounded growth habit. The male (pollen) parent of the new cultivar is the proprietary *Calibrachoa×hybrida* breeding selection coded 2333-4, not patented, characterized by its dark rose-colored flowers, medium green-colored foliage, and moderately vigorous, mounded growth habit. The new cultivar was discovered and selected as a single flowering plant within the progeny of the above stated cross-pollination during May 2009 in a controlled environment in Elburn, Ill.

Asexual reproduction of the new cultivar by terminal stem cuttings since May 2009 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcabpurim' as a new and distinct cultivar of *Calibrachoa* plant:

1. Deep purple-colored flowers;
2. Medium green-colored foliage; and
3. Moderately vigorous, trailing growth habit.

Plants of the new cultivar differ from plants of the female parent primarily in flower color and growth habit. Plants of the new cultivar differ from plants of the male parent primarily in flower color and growth habit.

Of the many commercially available *Calibrachoa* cultivars, the most similar in comparison to the new cultivar is CALLIE Purple 'Cal Pur07', U.S. Plant Pat. No. 19,278. However, in side by side comparisons, plants of the new cultivar differ from plants of 'Cal Pur07' in at least the following characteristics:

1. Plants of the new cultivar have a flower color that is darker than plants of 'Cal Pur07'; and
2. Plants of the new cultivar wider than plants of 'Cal Pur07'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcabpurim'. The plants were grown in 4.5-inch pots for 7 weeks in a greenhouse in West Chicago, Ill.

DETAILED BOTANICAL DESCRIPTION

Figure 1:
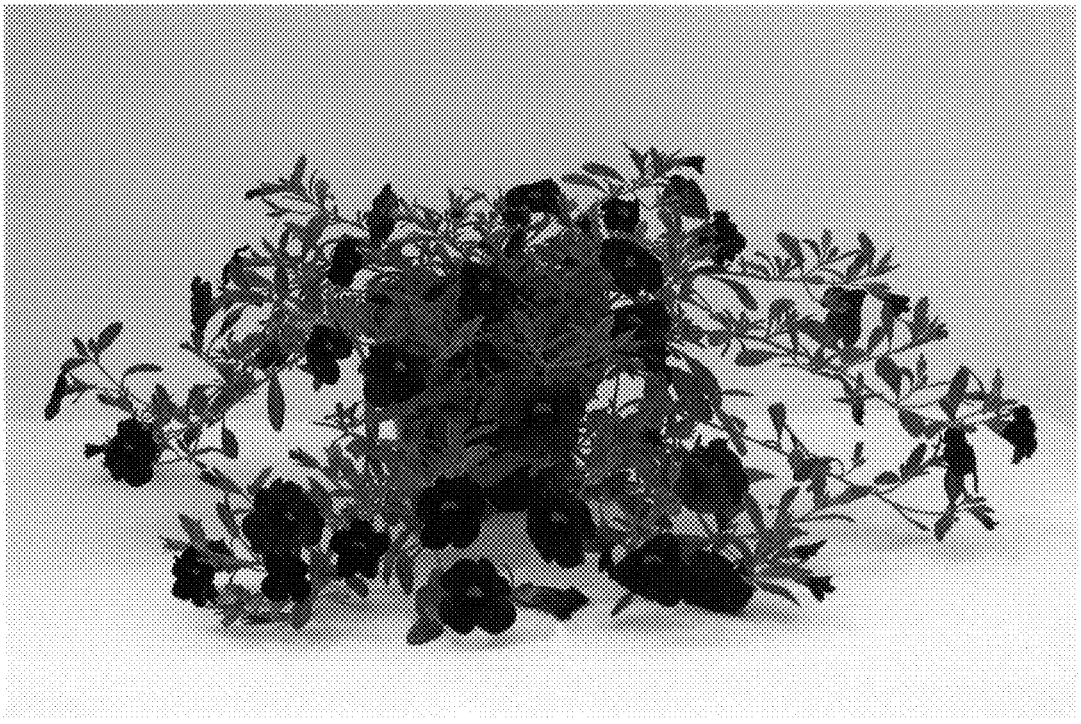
FIG. 1 illustrates a side view of the overall growth and flowering habit of 'Balcabpurim'.
Figure 2:
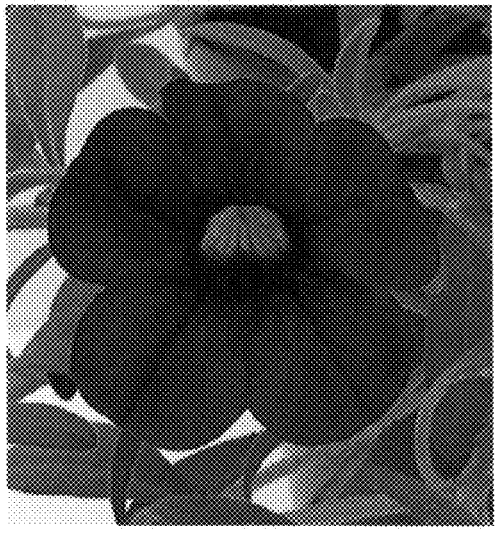
FIG. 2 illustrates a close-up view of an individual flower of 'Balcabpurim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2013 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Calibrachoa×hybrida* cultivar Balcabpurim.

Parentage:

*Female parent*.—Proprietary *Calibrachoa×hybrida* breeding selection coded 2296-10-1, not patented.

*Male parent*.—Proprietary *Calibrachoa×hybrida* breeding selection coded 2333-4, not patented.

Propagation:

*Type cutting*.—Terminal stem.

*Time to initiate roots*.—Approximately 6 to 8 days.

*Time to produce a rooted cutting*.—Approximately 24 to 28 days.

*Root description*.—Fibrous.

*Rooting habit*.—Freely branching.

Plant description:

*Commercial crop time*.—Approximately 6 to 7 weeks from a rooted cutting to finish in a 10 cm pot.

*Growth habit and general appearance*.—Moderately vigorous, trailing.

*Size*.—Height from soil level to top of plant plane: Approximately 7.3 cm. Width: Approximately 41.1 cm.

*Branching habit*.—Freely branching, pinching enhances basal branching. Quantity of main branches per plant: Approximately 6.

*Branch*.—Strength: Moderate. Length: Approximately 20.3 cm. Diameter: Approximately 2.0 mm. Length of central internode: Approximately 2.1 cm. Texture: Densely glandular pubescent. Gland color: Colorless, transparent. Color of young stem: 144A with an overlay of 187A. Color of mature stem: 144A with an overlay of 187A.

Foliage description:

*General description*.—Quantity of leaves per main branch: Approximately 20. Fragrance: Slight. Form: Simple. Arrangement on flowering stem: Opposite.

*Leaves*.—Aspect: At acute angle to stem with tip turning downward. Shape: Elliptic. Margin: Entire. Apex: Acute. Base: Attenuate. Venation pattern: Pinnate. Length of mature leaf: Approximately 3.0 cm. Width of mature leaf: Approximately 1.2 cm. Texture of upper surface: Moderately glandular pubescent. Texture of lower surface: Moderately glandular pubescent. Gland color: Colorless, transparent. Color of upper surface of young foliage: 137B with venation of 144D to indistinguishable. Color of lower surface of young foliage: 138A with venation of 138D to indistinguishable. Color of upper surface of mature foliage: 137A with venation of 144D to indistinguishable. Color of lower surface of mature foliage: 138B with venation of 138D to indistinguishable.

*Petiole*.—Length: Approximately 3.0 mm. Diameter: Approximately 1.0 mm. Texture: Moderately glandular pubescent. Gland color: Colorless, transparent. Color: 144D.

Flowering description:

*Flowering habit*.—'Balcabpurim' is freely flowering under outdoor growing conditions with substantially continuous blooming from spring through autumn and year-round in greenhouse environment.

*Lastingness of individual flower on the plant*.—Approximately 5 to 7 days.

Flower description:

*General description*.—Type: Single, salverform. Quantity per plant: Approximately 25. Fragrance: None detected.

*Bud*.—Rate of opening: Generally takes 3 to 4 days for bud to progress from first color to fully open flower. Quantity per plant: Approximately 19.

*Bud just before opening*.—Shape: Oblong. Length: Approximately 1.9 cm. Diameter: Approximately 5.0 mm. Texture: Densely glandular pubescent. Gland color: Colorless, transparent. Color: Petal portion darker than 83A and tube portion 151C, venation of N77A.

*Corolla*.—Diameter: Approximately 3.3 cm.

*Petals*.—Quantity: 5, fused to form a tube. Shape: Obovate. Margin: Entire. Apex: Obtuse. Length from tube: Approximately 1.2 cm. Length of free portion: Approximately 6.0 mm. Width: Approximately 1.5 cm. Texture of upper surface: Glabrous. Texture of lower surface: Glandular pubescent, dense along venation. Gland color: Colorless, transparent. Color of upper surface when first and fully open: Darker than but closest to 86A with midveins of N186A. Color of lower surface when first open: 83B with venation of 83A and midveins of N77A. Color of lower surface when fully open: 83B, fading with age to 83C; venation of 83A and midveins of N77A.

*Corolla tube*.—Length: Approximately 1.9 cm. Diameter at distal end: Approximately 6.0 mm. Diameter at proximal end: Approximately 2.0 mm. Texture of inner surface: Glabrous. Texture of outer surface: Densely glandular pubescent. Gland color: Colorless, transparent. Color of inner surface: N79A at tube opening transitioning to 13C with venation of N79A. Color of outer surface: 151D with venation of N77A.

*Sepals*.—Quantity per flower: 5, fused along lower half. Shape: Lanceolate. Apex: Acute. Length: Approximately 1.3 cm. Width: Approximately 2.0 mm. Texture of upper surface: Densely glandular pubescent. Texture of lower surface: Densely glandular pubescent. Gland color: Colorless, transparent . Color of upper surface: 137A. Color of lower surface: 138B with base of 144C.

*Peduncle*.—Strength: Strong. Aspect: Acute angle to stem. Length: Approximately 1.5 cm. Diameter: Approximately 1.0 mm. Texture: Densely glandular pubescent. Gland color: Colorless, transparent. Color: 144B with an overlay of 187A.

*Reproductive organs*.—Androecium: Stamen quantity: 5, basifixed. Stamen length: Approximately 1.0 cm.

Filament length of fixed portion: Approximately 4.0 mm. Filament color: 145D. Anther shape: Bilobed, ovoid. Anther length: Approximately 1.0 mm. Anther color: 8A. Pollen amount: Abundant. Pollen color: 8B. Gynoecium: Pistil quantity: 1 per flower. Pistil length: Approximately 1.1 cm. Stigma shape: Funnel. Stigma length: Less than 1.0 mm. Stigma color: 144A. Style length: Approximately 9.0 mm. Style color: N144D. Ovary diameter: Approximately 2.0 mm. Ovary color: N144C.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balcabpurim', substantially as herein shown and described.

* * * * *